United States Patent
Zdeblick et al.

(10) Patent No.: US 7,925,329 B2
(45) Date of Patent: Apr. 12, 2011

(54) IMPLANTABLE DOPPLER TOMOGRAPHY SYSTEM

(75) Inventors: Mark Zdeblick, Portola Valley, CA (US); George M. Savage, Portola Valley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 507 days.

(21) Appl. No.: 11/249,152

(22) Filed: Oct. 11, 2005

(65) Prior Publication Data

US 2006/0116581 A1 Jun. 1, 2006

Related U.S. Application Data

(60) Provisional application No. 60/617,618, filed on Oct. 8, 2004.

(51) Int. Cl.
*A61B 5/05* (2006.01)
(52) U.S. Cl. ......... 600/430; 600/374; 600/407; 600/505
(58) Field of Classification Search .................. 600/374, 600/508, 595, 407, 430
See application file for complete search history.

(56) References Cited

U.S. PATENT DOCUMENTS

| | | | |
|---|---|---|---|
| 4,182,315 A | 1/1980 | Vas et al. | |
| 5,243,976 A * | 9/1993 | Ferek-Petric et al. | 607/6 |
| 5,544,656 A | 8/1996 | Pitsillides et al. | |
| 5,628,777 A | 5/1997 | Moberg et al. | |
| 5,662,108 A | 9/1997 | Budd et al. | |
| 5,772,108 A | 6/1998 | Ruggiere, Sr. et al. | |
| 5,983,126 A | 11/1999 | Wittkampf | |
| 5,991,661 A | 11/1999 | Park et al. | |
| 6,002,963 A | 12/1999 | Mouchawar et al. | |
| 6,009,349 A | 12/1999 | Mouchawar et al. | |
| 6,026,325 A | 2/2000 | Weinberg et al. | |
| 6,044,299 A | 3/2000 | Nilsson | |
| 6,259,937 B1 | 7/2001 | Schulman et al. | |
| 6,263,248 B1 * | 7/2001 | Farley et al. | 607/98 |
| 6,295,464 B1 | 9/2001 | Metaxas | |
| 6,298,257 B1 | 10/2001 | Hall et al. | |
| 6,346,124 B1 | 2/2002 | Geiser et al. | |
| 6,477,406 B1 | 11/2002 | Turcott | |
| 6,493,575 B1 | 12/2002 | Kesten et al. | |
| 6,625,493 B2 | 9/2003 | Kroll et al. | |
| 6,731,970 B2 | 5/2004 | Schlossbauer et al. | |
| 6,795,732 B2 | 9/2004 | Stadler et al. | |

(Continued)

FOREIGN PATENT DOCUMENTS

EP 1321097 6/2003

(Continued)

OTHER PUBLICATIONS

Lee et al. "A Microprocessor-Based Noninvasive Arterial Pulse Wave Analyzer". IEEE Transactions on Biomedical Engineering 32(6) (1985): 451-455.*

(Continued)

*Primary Examiner* — Tse Chen
*Assistant Examiner* — Peter Luong
(74) *Attorney, Agent, or Firm* — Bret E. Field; Bozicevic Field & Francis LLP.

(57) ABSTRACT

The inventive implantable Doppler tomography system allows, for the first time, the use of Doppler shift for purposes of tracking cardiac wall motion. The present inventive Doppler tomography system methods and devices provide a critical new tool in the physician's armamentarium which provides accurate, real time monitoring of the mechanical performance of the heart.

20 Claims, 3 Drawing Sheets

U.S. PATENT DOCUMENTS

| | | |
|---|---|---|
| 6,889,084 B2 | 5/2005 | Thompson et al. |
| 6,950,689 B1 | 9/2005 | Willis et al. |
| 7,127,289 B2 * | 10/2006 | Yu et al. .............................. 607/9 |
| 7,130,681 B2 | 10/2006 | Gebhardt et al. |
| 7,263,398 B2 * | 8/2007 | Carr .............................. 600/430 |
| 7,269,460 B2 * | 9/2007 | Chinchoy ....................... 607/23 |
| 2003/0065365 A1 | 4/2003 | Zhu et al. |
| 2003/0100925 A1 | 5/2003 | Pape et al. |
| 2004/0077952 A1 | 4/2004 | Rafter et al. |
| 2004/0172078 A1 | 9/2004 | Chinchoy |
| 2004/0193021 A1 | 9/2004 | Zdeblick et al. |
| 2004/0243192 A1 | 12/2004 | Hepp et al. |
| 2005/0038481 A1 | 2/2005 | Chinchoy et al. |
| 2005/0043895 A1 | 2/2005 | Schechter |
| 2005/0215914 A1 | 9/2005 | Bornzin et al. |
| 2006/0004301 A1 | 1/2006 | Kasevich et al. |
| 2006/0058588 A1 | 3/2006 | Zdeblick |
| 2006/0116581 A1 | 6/2006 | Zdeblick et al. |
| 2006/0235480 A1 | 10/2006 | Schecter |
| 2007/0123944 A1 | 5/2007 | Zdeblick |
| 2007/0135721 A1 | 6/2007 | Zdeblick |
| 2007/0161894 A1 | 7/2007 | Zdeblick et al. |
| 2008/0058656 A1 | 3/2008 | Costello et al. |
| 2008/0183072 A1 | 7/2008 | Robertson et al. |
| 2008/0208068 A1 | 8/2008 | Robertson et al. |
| 2008/0294218 A1 | 11/2008 | Savage et al. |
| 2009/0036769 A1 | 2/2009 | Zdeblick |
| 2009/0148385 A1 | 6/2009 | Willard et al. |

FOREIGN PATENT DOCUMENTS

| | | |
|---|---|---|
| EP | 1503823 | 5/2006 |
| WO | 2003097160 | 11/2003 |
| WO | 2006029090 | 3/2006 |
| WO | 2006042039 | 4/2006 |
| WO | 2006069322 | 6/2006 |
| WO | 2006104869 | 10/2006 |
| WO | 2006105394 | 10/2006 |
| WO | 2006105474 | 10/2006 |
| WO | 2006113659 | 10/2006 |
| WO | 2007075974 | 7/2007 |

OTHER PUBLICATIONS

Iskander et al. "Electromagnetic Techniques for Medical Diagnosis: A Review". Proceedings of the IEEE 68(1) (1980): 126-133.*

"Implant." Merriam-Webster Online Dictionary. 2009. Merriam-Webster Online. Aug. 10, 2009. <http://www.merriam-webster.com/dictionary/implant>.*

Sermesant et al., "Stimulation of cardiac pathologies using an electromechanical biventricular model and XMR interventional imaging" Medical Image Analysis (2005) 9:467-480.

Sermesant et al., "An electromechanical model of the heart for image analysis and simulation" ISEE Transactions on Medical Imaging (2006) 25:612-625.

Usyk et al., "Electromechanical Model of Cardiac Resynchronization in the Dilated Failing Heart with Left Bundle Branch Block" J. Electrocardiology (supp 2003) 36: 57-61.

U.S. Appl. No. 12/522,537 filed Jul. 8, 2009; Arne et al., "Continuous Field Tomography Systems and Methods of Using the Same".

* cited by examiner

IMPLANTABLE DOPPLER TOMOGRAPHY SYSTEM

CROSS-REFERENCE TO RELATED APPLICATIONS

Pursuant to 35 U.S.C. §119 (e), this application claims priority to the filing date of: U.S. Provisional Patent Application Ser. No. 60/617,618 filed Oct. 8, 2004; the disclosure of which is herein incorporated by reference.

INTRODUCTION

The present Invention relates generally to medical methods, apparatus and systems. More specifically, the invention relates to methods, apparatus and systems for optimizing cardiac resynchronization intervention, arrhythmia management, ischemia ejection, coronary artery disease management, and heart failure management Cardiac resynchronization therapy is an important new medical intervention for patients suffering from congestive heart failure. In congestive heart failure, symptoms develop due to the inability of the heart to function sufficiently well as a mechanical pump to supply the body's physiologic needs. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time. Resynchronization therapy seeks to provide a contraction time sequence which will most effectively produce maximal cardiac output with minimal total energy expenditure by the heart. The optimal timing is calculated by reference to hemodynamic parameters such as dp/dt, the first derivative of the pressure waveform in the left ventricle. The dp/dt parameter is a well-documented proxy for left ventricular contractility.

In current practice, external ultrasound measurements are used to calculate the dp/dt. Such external ultrasound is used to observe wall motion directly. Most commonly, the ultrasound operator uses the ultrasound system in a tissue Doppler mode, a feature known as tissue Doppler imaging or TDI, to evaluate the time course of displacement of the septum relative to the left ventricle free wall. The current view of clinicians is that ultrasonographic evaluation using TDI or a similar approach may become an important part of qualifying patients for CRT therapy.

As currently delivered, CRT therapy is effective in about half to two-thirds of patients implanted with a resynchronization device. In approximately one third of these patients, this therapy provides a two-class improvement in patient symptoms as measured by the New York Heart Association fair level scale. In about one third of these patients, a one-class improvement in cardiovascular symptoms is accomplished. In the remaining third of patients, there is no improvement or, in a small minority, a deterioration in cardiac performance. This group of patients is referred to as non-responders. It is possible that the one-class New York Heart Association responders are actually marginal or partial responders to the therapy, given the dramatic results seen in a minority.

The synchronization therapy, in order to be optimal, targets the cardiac wall segment point of maximal delay, and advances the timing to synchronize contraction with an earlier contracting region of the heart, typically the septum. However, the current placement technique for CRT devices is usually empiric. A physician will cannulate a vein that appears to be in the region described by the literature as most effective. The device is then positioned, stimulation is carried out, and the lack of extra cardiac stimulation, such as diaphragmatic pacing, is confirmed. With the currently available techniques, rarely is there time or means to attempt to optimize cardiac performance.

When attempted today, CRT optimization must be preformed by laborious manual method of an ultrasonographer evaluating cardiac wall motion at different lead positions and different interventricular delay (IVD) settings. The IVD is the ability of pacemakers to be set up with different timing on the pacing pulse that goes to the right ventricle versus the left ventricle. In addition, all pacemakers have the ability to vary the atrio-ventricular delay, that is the delay between stimulation of the atria and the ventricle or ventricles themselves. These settings can be important in addition to the location of the left ventricular stimulating electrode is itself in resynchronizing the patient.

Some research efforts to assess cardiac motion through internal sensors have been made (e.g. accelerometers). Pacesetter researchers have described use of epicardial accelerometry as an arrhythmia detection system. Kroll et al teach a positional accelerometer for rate control (U.S. Pat. No. 6,625, 493, issued Sep. 23, 2003). Mouchawar et al provides cardiac wall motion detection using an accelerometer for detection of arrhythmias (U.S. Pat. No. 6,002,963, issued Dec. 14, 1999). Park et al teach use of an accelerometer for rate adaptive pacing (U.S. Pat. No. 5,991,661, issued Nov. 23, 1999). Nilsson describes an in-can accelerometer to provide rate control (U.S. Pat. No. 6,044,299, issued Mar. 28, 2000).

Some researchers have reported the use of position sensors deployed along different aspects of the heart with the intent of delivering relative position with the aim of describing the extent of myocardial contraction and effectively duplicating a portion of the information provided typically through ultrasonographic means in the clinic today. Such parameters include ejection fraction, stroke volume, cardiac output, and synchronization index. These systems again use a fixed frame of reference using ultrasonographic, magnetic or RF fields in orthogonal planes to generate a signal which can localize a catheter or catheters within the heart.

Current use of Doppler to localize elements in the heart have been limited to wall position determination via external ultrasonography, typically for purposes of measuring valve function, cardiac output, or rarely, synchronization index.

There is currently no useful clinically available means of determining optimal CRT settings on a substantially automatic or a real-time, machine readable basis. It would be an important advancement in cardiology to have an implantable means of monitoring the mechanical performance of the heart in real time, an immediate application being in setting the functions of cardiac resynchronization therapy pacemakers with further application to the pharmacologic management of heart failure patients, arrhythmia detection and ischemia detection.

SUMMARY OF THE INVENTION

The inventive implantable Doppler tomography system allows, for the first time, the use of Doppler shift for purposes of tracking cardiac wall motion. The present inventive Doppler tomography system methods and devices provide a critical new tool in the physician's armamentarium which provides accurate, real time monitoring of the mechanical performance of the heart.

An immediate and particularly important application for this technological breakthrough is to provide the optimum function settings for cardiac resynchronization therapy pacemakers. Employing the present inventive device and method, optimal resynchronization can be accomplished on a manual basis using more basic embodiments of the present invention. Additionally, in more complex embodiments, the present invention provides optimal resynchronization data into the algorithm for automatic setting of cardiac resynchronization therapy pacemakers.

The immediate goal of the present invention is to obtain hemodynamic parameter data similar to that delivered by current external tissue Doppler imaging. The current use of Doppler in cardiac imaging is accomplished by an externally applied ultrasound beam which is used to create an image. This image can, on further processing, be employed to derive important hemodynamic parameters. These parameters can provide some indication of cardiac wall synchronicity important to optimizing clinical performance of a biventricular or cardiac resynchronization pacemaker.

The present inventive Doppler tomography system allows, for the first time, the availability of effective resynchronization intervention to the significant population of non-responding patients who currently do not benefit from this life-saving therapy.

The present innovation of employing one or more Doppler transmitters and/or sensors to describe wall motion for purposes of resynchronization of a cardiac resynchronization therapy device is unique. Therefore, additional applications of this critical tool to various clinical challenges will be appreciated by the clinicians, as will many unique approaches enabled by this new tool. For instance, the data could be provided directly to the physician's office for monitoring patent progress, and providing modification of pharmaceutical intervention without requiring patient travel. This would be particularly advantageous for patients in remote areas, or locations without access to skilled ultrasound technicians. Additionally, physicians would be able to monitor patients during normal daily activities, which could encourage heart failure patients to resume health promoting increase in physical exertion. In some cases, they would, for the first time, be able to undertake a program of increasingly active exercise that would increase the quality of their lives and improve their overall clinical improvement In the context of the present application, the term "Doppler transmitter/sensors" refers to a range of implantable features, that may be transmitters only, may be sensors only, or may have the capacity to serve both as a Doppler transmitter and sensor, either at alternate times or simultaneously. Included within this meaning is the use of existing electrodes or other cardiac elements which can serve in this capacity in the context of the overall inventive system. Thus, current available and/or implanted pacing or sensing electrodes can serve as Doppler transmitter/sensors within the inventive system even if they were not initially designed or implanted to serve in that capacity.

The Doppler tomography method of the present invention can be provided much in a manner analogous to ultrasound used in the clinical environment. Additional methods used in radar and in other applications for tracking the speed and position of everything from aircraft to automobiles to baseballs can be used in the present inventive methods.

By employing a variety of electrode pairs in the present Doppler tomography system, each broadcasting in a discrete frequency, multiple lines of position and velocity can be calculated from differing reference frames. This embodiment of the present invention creates a Doppler tomogram providing an enormous amount of clinically relevant velocity and positional information in real-time. As a major advancement over currently available clinical ultrasound methods, these data provided by the inventive Doppler tomography system would be inherently machine-useable as the positioning velocity data are numeric rather than an image requiring human interpretation with all the inconsistencies inherent in individual interpretation.

A further advantage of the inventive Doppler tomography system is that the influence of reflected signals from regions far from the area of interest is reduced. That is because the inventive system does not rely on reflected signals. Rather, the present system is informed by directly transmitting signals to a receiving electrode and/or electrodes located elsewhere in the heart, the body, or on the surface of the skin.

The present invention can be implemented in the practical deployment of multiple sensors to describe in further detail wall motion on a segmental basis. This novel platform multiplexed endocardial lead system is an innovation of some of the current inventors, and is described below with reference to co-pending and published applications.

DETAILED DESCRIPTION OF THE INVENTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The inventive Doppler tomography system invention uses electromagnetic energy preferentially to determine position of various cardiac structures. Unlike prior sensor approaches to providing data on cardiac wall position, the Doppler tomography system determines these positions by exploiting the Doppler frequency shift caused by relative motion of the cardiac walls with respect to various electrode pairs located intra or extracardiac. In the subject tomography methods, data obtained by a sensing element stably associated with the tissue location of interest as it moves through an applied continuous field are employed. While the methods may be viewed as tomography methods, such a characterization does not mean that the methods are necessarily employed to obtain a map of a given tissue location, such as a 2-dimensional or 3-dimensional map, but instead just that changes in a sensing element as it moves through an applied continuous field are used to evaluate or characterize a tissue location in some way.

One advantage of the inventive Doppler tomography techniques is that direct position information can be calculated by a single integration of the Doppler signal. This unique quality is in contrast to such sensor approaches as accelerometry which require double integration. A further advantage of the inventive Doppler tomography system is that direct relative velocity, which can be very valuable in optimizing biventricular pacing, is immediately available from the Doppler signal or signals themselves.

Using the present Doppler tomography system, if direct range information is desired, the range and velocity information can be obtained simultaneously. This is accomplished by employment of a pulse technique. Using this technique, the fundamental frequency is transmitted in a pulse nature such that time of flight to the receiving electrode can be calculated. This calculation provides the ability to determine range while simultaneously determining the Doppler frequency shift. In this manner; the relative line of site velocity information is provided.

The Doppler tomography method of the present invention is in some ways similar to ultrasound used in the clinical environment. However, by employing a variety of electrode pairs in the present Doppler tomography system, each broadcasting in a discrete frequency, multiple lines of position and velocity can be calculated from differing reference frames. Thus, a Doppler tomogram is created. This unique data providing, for the first time, clinically relevant velocity and positional information in real time. This data is inherently machine-useable as the positioning velocity data are numeric rather than an image requiring human interpretation with all the inconsistencies inherent in individual interpretation. The present system is informed by directly transmitting signals to a receiving electrode located elsewhere in the heart.

In biventricular or cardiac resynchronization pacing applications of the present Doppler tomography invention, a single number is provided whereby the Doppler signal itself is maximized. In this embodiment of the present invention, the maximum positive frequency shift indicates maximal synchrony between a lead. For instance, a lead positioned against the right ventricular septum as compared with another lead with electrodes positioned in an optimal cardiac vein located in the epicardial aspect of the left ventricular free wall will provide the necessary information.

In the present invention, a maximal Doppler shift during systole in the positive or higher frequency direction indicates maximal relative motion inward between the two components. To optimize the use of the data obtained by the present invention, an additional embodiment can include correlating this data with data from a pressure sensor. This pressure can be located in either the right or left ventricle or nearby in another area such as the aorta. Thus, this embodiment of the present invention include coordinating data provided by a pressure sensor indicating systolic performance with the wall motion data providing improved hemodynamic performance for congestive heart failure patients.

By adding a pulsing feature and time of flight information to the Doppler component of the present invention, direct positional information (i.e. not requiring integration of the Doppler signal) is added to the mix of information. In this manner, synchrony is assessed between various parameters such as a dp/dt, the first derivative of the pressure curve correlated to maximal relative velocity during systole towards the center of the ventricle. Also provided is the actual maximum position of displacement on a net basis of the monitored wall segments towards the center.

The optimal mix of these various parameters, which will be readily determinable by the practitioner, allows for calibration of the optimal stimulation location or locations in the setting of CRT. It also provides for optimal timing of the sequence of atrial ventricular and ventricle to ventricular delay timings. In addition, multiple electrodes are stimulated in a pattern and in manners previously unavailable to the clinician and as yet undescribed due to the current unavailability of the inventive optimization and feedback system.

Additional applications for the inventive sensor include applications as an ischemia detector. It is well understood that, before biochemical or electrical markers of cardiac ischemia present themselves, wall motion is first affected with the ischemic region showing increased stiffness and decreased contraction. These sorts of changes can be readily detected by the system currently invented.

The inventive Doppler tomography system can serve as an arrhythmia detector. Currently implantable defibrillator systems are challenged by differentiating between a variety of benign and malignant arrhythmias relying as they do primarily on electrical means of discrimination. Mechanical means, such as the wall motion positional detector, which is the subject of the current invention, would mark a significant advantage in detecting arrhythmias.

In the management of congestive heart failure patients, the inventive Doppler Tomography System has clinical capacity well beyond the needs of optimizing either on a one-off basis or dynamically as part of a closed loop feedback system for biventricular pacing. The Invented Doppler Tomography System can be effectively employed by specialists, such as congestive heart failure cardiologists, to address a patient's medication, diet and exercise regimen in response to real time physiologic data such as ejection fraction, stroke volume, and cardiac output which may be determined employing such a system.

The totally implantable system embodiment of the present invention which includes intracardiac leads and other structures utilizing the Doppler shift can be further modified in another embodiment of the present invention if relative positional data from such a system prove inadequate for certain cardiovascular applications. This capacity can be added through the addition of extracardiac electrodes transmitting RF pulse signals.

Extracardiac electrodes can be located either in the subcutaneous location or via adhesive cutaneous electrodes on a temporary basis when visiting the clinic. Temporary application can be made through placement of adhesive skin electrodes. Extracardiac electrodes as part of the present inventive system transmit additional frequencies. These transmissions provide an extracardiac frame of reference for precisely localizing the implanted elements. The localization made available for the first time by the present invention are not limited to a relative basis but provided in an absolute basis. This inventive advancement permits greater accuracy in the determination of various physiologic parameters such as ejection fractions, stroke volume, cardiac output and others with enhanced accuracy.

With sufficient lines of position provided in various embodiment of the present invention through utilization of sufficient number of electrode pairs on the intracardiac components, Doppler tomography itself can be used to resolve absolute position. This can be accomplished using the invention approach even when all parts are moving relative to one another.

The central principle being used by the present inventive Doppler tomography system is to obtain positional and velocity information is the Doppler shift. This phenomena has been well characterized and applied to all forms of electromagnetic radiation as well as acoustic radiation. The standard formula states the change in wavelength observed due to relative motion equals the wavelength first injected into the system multiplied by the velocity vector directly towards the transmitter and or receiving system divided by the conduction velocity of the waveform in the material of interest. For example, in the case of radar guns used in the air, that speed would be approximately the speed of light. This principle in the present invention is applied for radio waves that are transmitted by the inventive Doppler transmission/sensor units.

In a preferred embodiment of the current invention, the conduction velocity would be via ionic conductance of an applied RF signal in the body. Consistent with data developed by the present inventor, this conductance velocity is approximately 10% to 15% the speed of light in physiologic normal saline.

Other embodiments of the present invention employ sufficiently high frequencies and small antennae designs embedded in the intracardiac catheter that a light speed radiated signal is used. Other embodiments include ultrasound transducers for converting the applied electrical signal into acoustic energy. In this case, the acoustic energy is then received by the receiving transducer. The signal is then recorded in that means and using the speed of sound in the human body as the conduction velocity, the relevant information calculated using the Doppler formula.

In the initially preferred embodiment of the present invention, radio frequency energy is delivered at low power and transmitted via conductance. Each emitting electrode pair is also potentially a receiver. As a result, each pair of electrodes is capable of both broadcasting a pulse, and can also either simultaneously or at a different time receive pulses from the various other transmitting electrodes. The frequency bands are sufficiently separated such that the received time delay and frequency shift could be accurately recorded and its source determined.

In additional embodiments of the present invention, computation ornaments are added to the system even on an implantable basis for full time analysis or via download or real time interrogation on an external basis in order to compute the parameters of interest at any given time.

Doppler shift has not yet been reported or used in the context of an implantable cardiac device. The current invention offers both a solid state and constructible, reliable means of optimizing biventricular pacing both in terms of location and timing. This allows prompt detection of reversible and irreversible ischemia, especially so-called "silent ischemia". The invention also allows a determination of important hemodynamic parameters on a permanent implantable basis. Such hemodynamic parameters can include such components as stroke volume, ejection fraction, cardiac output and others, as well arrhythmia detection and classification via reliable mechanical means.

The manufacturer of the inventive Doppler transmitter/sensor point has particular advantages over other sensors. Active devices such as accelerometers can be difficult to fabricate. This difficulty is particularly accentuated in the very small sizes required for incorporation into implantable leads or other means of intracardiac implantation. Furthermore, hermetically sealing such devices from the corrosive environment of the body is problematic. Additionally, delivering power and data in reliable fashion to such sensors adds to the challenge of producing a highly robust system.

A benefit of the current inventive Doppler tomography system is that conventional intracardiac electrodes can be used. In fact, electrodes used in the inventive system may be the same electrodes used for other purposes. By example, electrodes used in cardiac sensing of ECG, cardiac pacing and delivery of defibrillation pulses can be employed. Since these other activities of the electrodes occur on significantly different frequencies from the Doppler methodology of the present invention, no interference would occur between the multiple purposes to which such electrodes could be used.

If ionic conduction velocity is selected in an embodiment of the present invention rather than free spatial electromagnetic radiation, a calibration of conduction velocity may, in some instances, be required. One approach to these challenges is to time a pulse transmission crossing distance such as the distance between electrode pairs on an implantable device such as an implantable lead. If ionic conduction velocity were found to vary significantly between blood and tissue, correction factors can be incorporated in order to reduce the noise inherent in the data. Alternatively, this factor could be omitted if such conduction velocity differences were not significant as compared to the signal itself.

The devices of the present invention may be fabricated to utilize frequencies in the acoustic domain such as ultrasound transducers or small antennae utilizing free space radiation in a very high frequency domain. In the case that multipath signals caused by multiple reflections are a limiting factor, processing power and selective filtering would ameliorate these effects. Therefore a preferred embodiment of the inventive Doppler tomography system is to use the lower frequencies associated with ionic conduction in order to simplify the initial application of the invention.

One important distinguishing feature of the present invention is that, unlike radar or external beam ultrasound, the current invention does not rely upon reflected energy returning to the emitter in order to acquire data. Instead, the invention relies upon primary emissions from electrode pairs or other transducers being received by transducers in a receiving mode located at another location.

Using the devices and methods of the present invention, the timing and displacement of contraction of the monitored sections of the heart can be compared to one another, phase and amplitude differences evaluated, and means manually or automatically taken to move contraction of wall segments into synchronization with one another. In this way, the maximum contraction occurs at essentially the same time or the time most efficient from the standpoint of producing the greatest hemodynamic output for the least amount of effort.

In one embodiment of the present invention, the critical resynchronization data is obtained by means of localizing endocardial elements along the right ventricular septum and an aspect of the left ventricle. This can be accomplished, either by the endocardial approach through a cardiac vein, or through an epicardial approach analogous to placement of an epicardial left ventricular stimulation electrode. The inventive device in this case is configured to describe the relative position of the different wall segments relative to one another.

A preferred embodiment of this approach would involve the placement of one or more Doppler transmitters/sensors along a lead located in close association with the right ventricular septum, and also in addition, a lead located in a cardiac vein located on the left ventricular surface. An alternative would include a lead using Doppler transmitter/sensors placed in the antero-septal vein that roughly tracks the inter ventricular septum and another further laterally or posteriorly along the left ventricular surface.

In another aspect of the present invention, additional Doppler transmitter/sensors are place along the aspect of the right ventricular free wall. This provides an understanding of interventricular disynchrony, rather than intraventricular dysynchrony within the left ventricle itself. These data are particularly useful in cases of both right ventricular heart failure and right-sided heart failure.

Use of the present inventive Doppler transmitter/sensor based systems can be usefully coordinated with other positional sensors. These additional positional sensors include electromagnetic methods such as tuned circuits, Hall effect sensors, time-of-flight sensors, accelerometer, and ultrasonographic methods. The coordinated use of these various positional sensors can be accomplished using a number of different approaches. For example, a multi-electrode left ventricular pacing lead can automatically select the optimal electrode and optimal timing sequence within a predetermined range selected by the physician using important hemodynamic parameters indicative of resynchronization.

Such alternative sensors have been described in various applications by some of the present inventors. These applications as also describe multiplexing systems previously developed by some of the present inventors with which the present invention is very usefully employed. In this prior work by some of the present inventors is described the use of dimension sensors for resynchronization. This system is described in part in currently pending patent applications U.S. Pat. No. 7,200,439 entitled "Method and Apparatus for Enhancing Cardiac Pacing", U.S. Pat. No. 7,204,798 entitled "Methods and Systems for Measuring Cardiac Parameters", and U.S. Pat. No. 7,267,649 entitled "Method and System for Remote Hemodynamic Monitoring" all filed Jan. 23, 2004, and U.S. patent application Ser. No. 10/734,490 entitled "Method and System for Monitoring and Treating Hemodynamic Parameters" filed Dec. 11, 2003. These applications are herein incorporated into the present application by reference in their entirety.

These additional positional sensor can include but are not limited to, electromagnetic methods such as tuned circuits, Hall effect sensors, time of flight sensors, accelerometers and ultrasonographic methods.

Other derived hemodynamic parameters similar to those obtained in ultrasound will be recognized by the artisan. In an additional embodiment of the present invention, additional sensors deployed along other areas of the heart in multiple planes provide data that will provide a complete characterization of the function of the ventricle or ventricles. This wealth of real time information can be provided continuously to the clinician on a permanent implantable basis. This ongoing position data can also be provided to the pacing system controller directly. This allows automated optimization of pacing timing and to which electrodes pacing will prove most clinically beneficial.

Recently, Overall et. al. has described the concept of using apical accelerometry and other sensors to detect heart ischemia by detecting abnormalities in motion (WO 2004/066825 A2, published Aug. 12, 2004).

As described above, an important application of the present invention is in cardiac resynchronization, or CRT, also termed biventricular pacing. The CRT technique has proven effective in relieving symptoms, improving quality of life, and prolonging life in selected congestive heart failure patients. Currently, CRT therapy is medically indicated in approximately 15% of the CRT population. This population is defined as patients suffering from moderate to severe heart failure, New York Heart Association Class III/IV, a prolonged QRS interval of greater than 150 ms, an enlarged left ventricle, and a left ventricular endostolic dimension of 50 mm or greater.

Cardiac resynchronization therapy attempts to remedy the delayed left ventricular mechanics of heart failure patients. In a desynchronized heart, the interventricular septum will often contract ahead of portions of the free wall of the left ventricle. In such a situation, where the time course of ventricular contraction is prolonged, the aggregate amount of work performed by the left ventricle against the intraventricular pressure is substantial. However, the actual work delivered on the body in the form of stroke volume and effective cardiac output is lower than would otherwise be expected.

Biventricular pacing therapy typically introduces pacing leads in the right atrium, right ventricle, and the left ventricle. 90% of such patients have the left ventricular lead placed via the right side of the heart. The endovascular method accesses the coronary sinus and thence along the coronary sinus to a branch of the cardiac vein. The preferential position is along the lateral or posterior-lateral aspect of the left ventricular free wall.

In approximately 10-15% of patients, adequate cardiac venous access for introduction of pacing leads is not available. In these cases, left ventricular stimulation must be performed via placement of an epicardial lead, usually via a minimally invasive surgical procedure.

CRT is the first device-based therapy for CHF which has been demonstrated to improve patient quality of life. It has been characterized by extremely rapid growth in number of units implanted since its introduction. However there are disadvantages to this therapy as currently administered.

The first is that it is very expensive, with the average price for CRT systems in the field being approximately $32,000, and in some cases higher. This price is for very capable systems which incorporate anti-tachycardia and ventricular fibrillation therapies such as anti-tachycardia pacing and defibrillation to save the patient in the event of a lethal arrhythmia in addition to the beneficial resynchronization pacing.

As currently practiced, external ultrasound measurements are used to calculate the dp/dt. Such external ultrasound is used by the clinician to directly observe wall motion. Each ultrasound operator uses the ultrasound system in a tissue Doppler mode, a feature known as tissue Doppler imaging or TDI, to evaluate the time course of displacement of the septum relative to the left ventricle. In this case, a desynchronized heart will develop a dyskinetic motion of part of the ventricle relative to another. As a result, as the septum contracts, the clinician can observe that the left ventricle free wall ventricle, far from contracting, actually move outwards in the direction opposite appropriate function. The mechanical effect of this is to move a portion of the left ventricular blood from one side to the other rather than effectively squeezing it outward into the aorta as required for optimized function.

The present invention represents an important advancement in resynchronization intervention if the population of patients who could benefit from this therapy could be extended well beyond the current group of CHF responders to this therapy. There is a growing realization in cardiac medicine that QRS interval may be a non-optimal criteria to rely upon in resynchronization patients. A prolonged QRS represents slow electrical depolarization of the heart, electrical disynchrony, which often, but does not always, correlate to mechanical disynchrony. There is growing appreciation that a large number of patients have mechanical disynchrony in the setting of a normal QRS interval. These patients display a normal depolarization event followed by a variable response to that depolarization event in terms of the timing sequence of ventricular contraction.

A preferred embodiment of the present invention is configured as an implantable system with either a can, hermetically sealed can with a battery and processing gear, or a coil designed for subcutaneous placement. With this inventive configuration, power and data can be transmitted through the skin to the device. Two leads extend from the inventive device. One of these leads is placed in the right ventricle in close association with the interventricular septum. The second lead is positioned to access the coronary sinus by being placed along another aspect of the left ventricle through a cardiac vein. Alternatively, the leads can be positioned in a manner analogous to the cardiac resynchronization therapy process. For instance, a left ventricular lead could be placed epicardially if suitable cardiac veins are not available for cannulation.

The system can be configured with Doppler shift sensors along each lead or an alternative position detector, such as a radio frequency or tuned circuit or Hall effect or time of flight sensor, such that the relative position of the sensors one from another can be determined throughout the course of the cardiac cycle.

The subject methods may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

Figure 1:
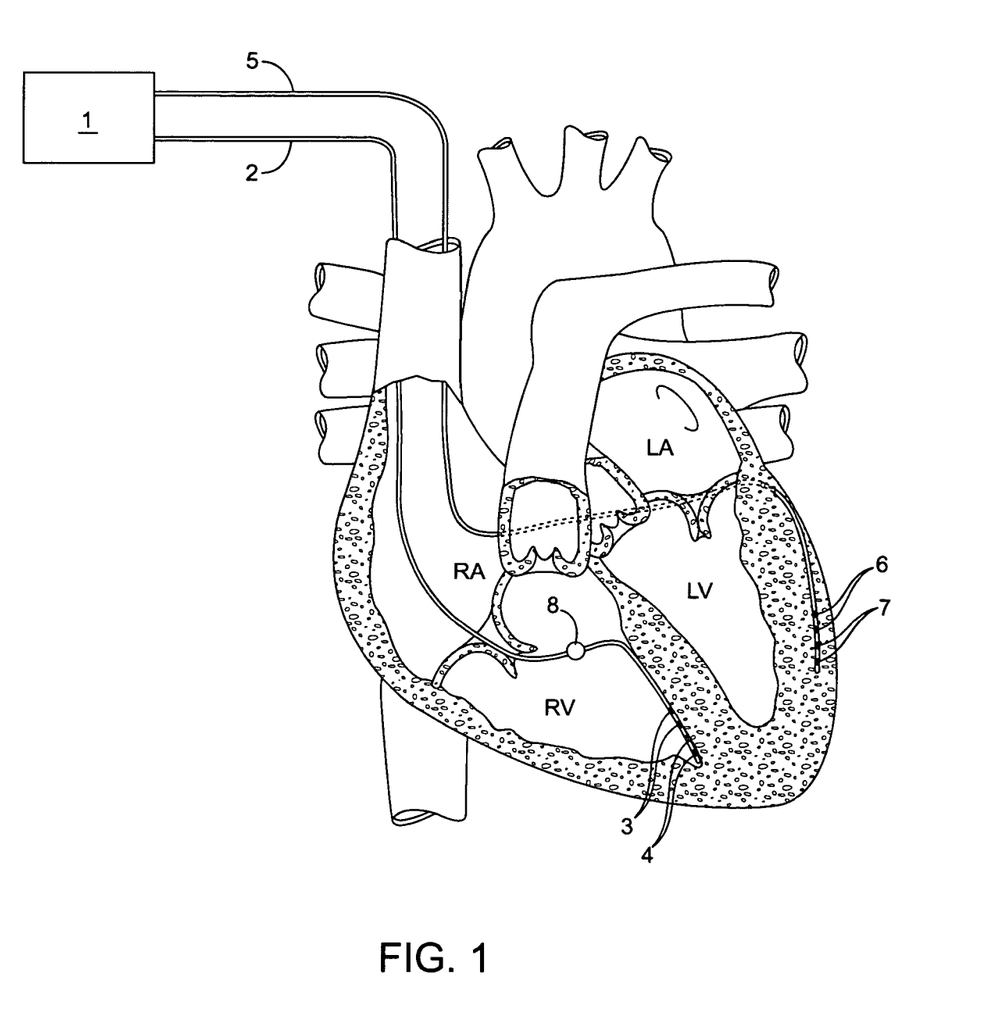
FIG. 1 provides a diagram of a preferred embodiment of the inventive implantable Doppler tomography system.

FIG. 1 provides a diagrammatic view of a preferred embodiment of the inventive implantable Doppler tomography system. Communication means 1 provides the extracardiac communication and calculation means for the overall system. Communication means 1 can take the form of various embodiments including an implantable device complete with power supply, drive electronics and processing power on board. In more complex configurations, communication means 1 may provide a means for communicating data and power from a completely external or extracorporeal location.

Right ventricular lead 2 emerges from communication device in communication means 1, and travels from the preferentially subcutaneous location of communication means 1 via the subclavian venous access through the superior vena cava through the right atrium and then through the tricuspid valve to a position along the right ventricle. This location is preferentially located along its distal portion in close association with the intraventricular septum terminating distally with fixation in the right ventricular apex.

Particular to distal aspect of right ventricular lead 2 are right ventricular electrode pairs 3 and 4. In other embodiments of the present invention, an additional number or smaller number of electrodes may be employed.

Additionally emerging at the proximal aspect of communication means 1 is left ventricular lead 5. Left ventricular lead 5 starts by following the same route as right ventricular lead 2 via subclavian vein through the superior vena cava into the right atrium. At this point, left ventricular lead 5 is placed via the coronary sinus around the posterior aspect of the heart and thence into cardiac vein draining into said sinus.

FIG. 1 further depicts left ventricular lead 5 in a position likely to be advantageous for biventricular pacing located along the lateral aspect of the left ventricle. Left ventricular electrode pairs 6 and 7 are shown in this drawing analogous to electrode pairs three and four which are previously described.

Right ventricular lead 2 may optionally be provided with pressure sensor 8 which is located in the right ventricle. Pressure sensor 8 provides a pressure signal which can also simultaneously be obtained with wall motion data. It is notable that adding active devices to said lead such as pressure sensor 8 is facilitated through use of a multiplexing system, which has been previously disclosed and may or may not be used in this case.

Principle of operation of the inventive implantable Doppler tomography system is that a communication means 1 will either communicate or generate a radio frequency at different frequencies. By, example a 30 kilohertz signal can be provided with a 100 or 200 kilohertz shift for each successive electrode pair. Those frequencies can be delivered in a pulse mode with a clock used to determine the onset of the pulse, pulse transmission being delivered, and then detection of being timed for the various electrode pairs other than the originating emitting pair. That time of flight would, if a pulse were originating for example on right ventricular electrode pair 3 would be used to calibrate time of flight by reference to receipt time on right ventricular electrode pair 4 which is a known distance distal from right ventricular electrode pair 3 on right ventricular lead 2. Time of flight of the pulse emitted to left ventricular electrode pairs 6 and 7 provides instantaneous range information as to the relative distance between the emitting and receiving electrode pairs.

Simultaneously, in the current example of the pulse received at left ventricular electrode pairs 6 and 7 would be routed back to communication means 1 and the originating frequency subtracted from the received frequency using the mixer.

The resulting frequency would represent the frequency shift and that could be used via the Doppler formula to calculate the instantaneous velocity. Processing of this data could also resolve position by integration. Performing the first derivative of this data could also yield acceleration information.

Figure 2:
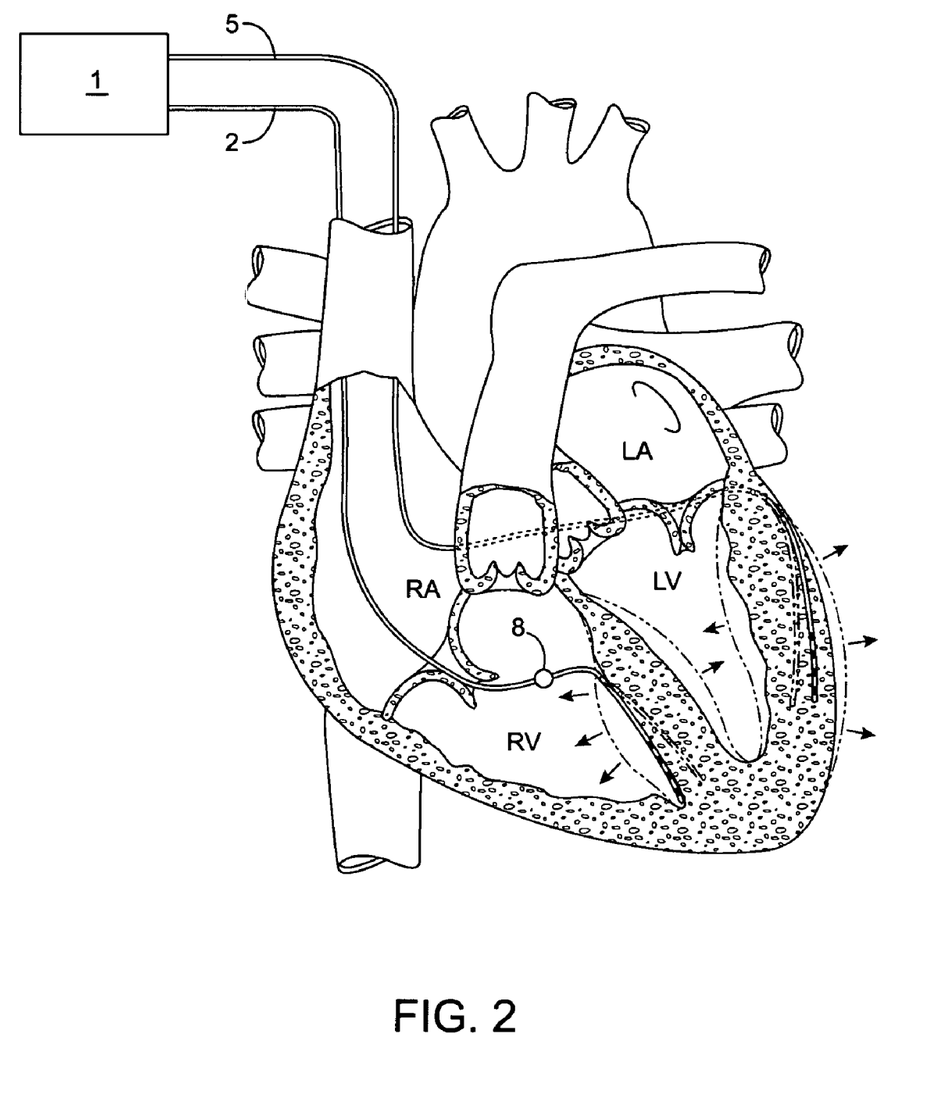
FIG. 2 provides a diagram of an additional preferred embodiment of the inventive implantable Doppler tomography system.

FIG. 2 depicts the roles of the heart in motion. With a lead such as right ventricular lead 2 and left ventricular lead 5 in close association with the wall of the heart as the wall of the heart moved via 3D cardiac cycle and so would the catheters in a proportionate amount. As these catheters moved towards and away from one another, the range and velocity information derived from the aforementioned method would shift over the course of the cardiac cycle in a manner indicative of their movement and timing of said movement.

The position data and extent of the Doppler shift together with an optional pressure signal or signals is used to optimize cardiac resynchronization therapy where the goal is to maximize the contractility of the left ventricle. This is obtained by encouraging effectively simultaneous contraction of the bulk of the muscle of the left ventricle. In many congestive heart failure patients, such contractility is impaired with dyskinetic contraction often occurring typically septal contraction against a relaxed left ventricle followed by ventricular contraction against a relaxing septum, the result being inefficiency with regards to blood being moved around the ventricle rather than constrictively expelled from the ventricle as in a normal human dynamic case.

Current systems provide biventricular pacing on an empiric basis only where optimization is attempted. It is generally a time-consuming process relying on external cardiac ultrasound with a physician attempting to visualize wall motion and with the aid of tools in the ultrasound machine calculating a synchronicity index based on the wall motion just described. The current system would provide such data in real time and in a numeric format useable by both the implanting physician and by an automated pacing system such as a CRT device.

The inventive implantable Doppler tomography system can detect abnormalities in wall motion associated with ischemia or arrhythmia and other cardiac abnormalities including progression of underlying disease states such as congestive heart failure. If connected to an external or fully implanted real time monitor, such abnormalities could trigger an alarm which can be used to alert the patient and or their physician.

Figure 3:
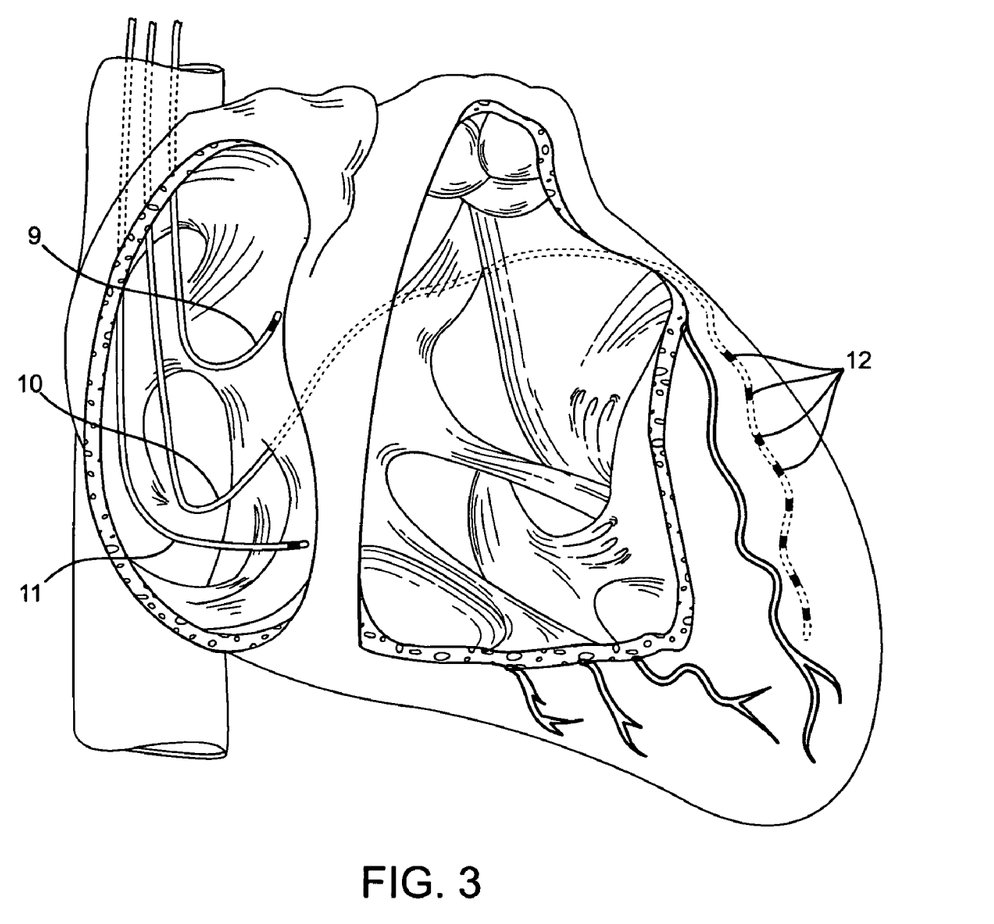
FIG. 3 provides a three dimensional cutaway view of placement of the inventive Doppler tomography system in the left ventricle.

FIG. 3 shows the posterior aspect of the heart. In this case, three leads are depicted which would be the typical state in a biventricular pacing system in which the current invention could be integrated in another preferred embodiment.

Depicted graphically in right atrial lead 9 is a right atrial pacing lead. A left ventricular lead 10 is depicted entering the coronary sinus and then the dash lines indicting passage through the coronary sinus and thence along a cardiac via the interior of a cardiac vein along the left ventricular surface. Right ventricular lead 11, while not shown the current view, is preferential positioned intimately along the intraventricular septum.

By means of VCR and the various electrodes 12 along the left ventricular lead 10 would be each of these being used potentially for pacing as well as for Doppler shift related position and velocity information according to the manner just described. This information could be taken relative one to another to give a sense for local left ventricular shortening as well as relative to the electrodes located in the right atrium and right ventricle. The additional electrodes could be placed at the subcutaneous implantation site of an implantable pulse generator or coil.

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means.

More specifically, computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s).

Of particular interest in certain embodiments are systems loaded with such computer readable mediums such that the systems are configured to practice the subject methods.

Also provided are kits for use in practicing the subject methods. The kits at least include a computer readable medium, as described above. The computer readable medium may be a component of other devices or systems, or components thereof, in the kit, such as an adaptor module, a pacemaker, etc. The kits and systems may also include a number of optional components that find use with the subject energy sources, including but not limited to, implantation devices, etc.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

As is evident from the above results and discussion, the subject invention provides numerous advantages. Advantages of the subject invention include the ability to obtain inherently computer useable data in real time, e.g., to provide for superior therapeutic and/or diagnostic methods, e.g., CRT methods. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of an implantable Doppler tomography system for describing movement of tissue locations in a subject, the method comprising:
   (a) transmitting electromagnetic energy from a transmitter configured on a first implantable lead of the implantable Doppler tomography system, wherein the transmitter is stably associated with a first tissue location in the subject when the first implantable lead is placed along the first tissue location;
   (b) directly detecting the electromagnetic energy at a sensor configured on a second implantable lead of the implantable Doppler tomography system, wherein the sensor is stably associated with a second tissue location in the subject when the second implantable lead is placed along the second tissue location;
   (c) determining a Doppler shift in the electromagnetic energy received at the sensor using a signal processing element of the implantable Doppler tomography system; and
   (d) providing data associated with a movement of the second tissue location relative to the first tissue location based on the Doppler shift in the electromagnetic energy received at the sensor.

2. The method according to claim 1, wherein the electromagnetic energy is an RF field.

3. The method according to claim 1, wherein the transmitter and sensor are electrodes.

4. The method according to claim 1, wherein the transmitter transmits the electromagnetic energy in a pulse mode.

5. The method according to claim 1, wherein each of the first tissue location and the second tissue location is a cardiac location.

6. The method according to claim 5, wherein the cardiac location is a heart wall location.

7. The method according to claim 6, wherein the heart wall is a chamber wall.

8. The method according to claim 7, wherein the chamber wall is a ventricular wall.

9. The method according to claim 8, wherein the ventricular wall is a septal wall.

10. The method according to claim 1, wherein the first tissue location is on a first cardiac wall and the second tissue location is on a second cardiac wall.

11. The method according to claim 10, wherein the providing the data comprises determining a motion of the first cardiac wall relative to the second cardiac wall based on the Doppler shift.

12. The method according to claim 11, wherein the providing the data further comprises determining timing of the motion of the first cardiac wall relative to the motion of the second cardiac wall based on the Doppler shift.

13. The method according to claim 12, further comprising detecting ventricular mechanical dyssynchrony based on the Doppler shift.

14. The method according to claim 13, wherein the ventricular mechanical dyssynchrony is interventricular.

15. The method according to claim 13, wherein the ventricular mechanical dyssynchrony is intraventricular.

16. The method according to claim 13, further comprising performing cardiac resynchronization therapy based on an outcome of the ventricular mechanical dyssynchrony.

17. A system for describing movement of tissue locations in a subject, the system comprising:
   (a) a first implantable lead and a second implantable lead;
   (b) an electromagnetic energy transmitter configured on the first implantable lead and to transmit electromagnetic energy, wherein the electromagnetic energy transmitter is adapted to be stably associated with a first tissue location in the subject when the first implantable lead is placed along the first tissue location;
   (c) an implantable sensing element configured on the second implantable lead and to detect the electromagnetic energy, wherein the implantable sensing element is adapted to be stably associated with a second tissue location in the subject when the second implantable lead is placed along the second tissue location; and
   (d) a signal processing element communicatively coupled to the electromagnetic energy transmitter and the implantable sensing element and configured to determine a Doppler shift in the electromagnetic energy detected at the implantable sensing element and to provide data associated with a movement of the second tissue location relative to the first tissue location based on the Doppler shift.

18. The system according to claim 17, further comprising a cardiac electrical stimulation element.

19. The system according to claim 18, further comprising a cardiac resynchronization therapy element.

20. A non-transitory computer readable storage medium having a processing program stored thereon, wherein the processing program operates a processor to operate a system comprising:
   a first implantable lead and a second implantable lead;
   an electromagnetic energy transmitter configured on the first implantable lead, wherein the electromagnetic energy transmitter is adapted to be stably associated with a first tissue location in the subject when the first implantable lead is placed along the first tissue location;
   an implantable sensing element configured on the second implantable lead, wherein the implantable sensing element is adapted to be stably associated with a second tissue location in the subject when the second implantable lead is placed along the second tissue location; and
   a signal processing element communicatively coupled to the electromagnetic energy transmitter and the implantable sensing element, and wherein the processing program to perform a method comprising:
   transmitting electromagnetic energy from the electromagnetic energy transmitter;
   directly detecting the electromagnetic energy at the implantable sensing element; and
   using the signal processing element, determining a Doppler shift in the electromagnetic energy received at the implantable sensing element and providing data associated with a movement of the second tissue location relative to the first tissue location based on the Doppler shift.

* * * * *